United States Patent [19]

Fujiwara et al.

[11] Patent Number: 5,572,032
[45] Date of Patent: Nov. 5, 1996

[54] GAS ANALYZER AND GAS-ANALYZING MECHANISM

[75] Inventors: Masahiko Fujiwara; Shigeyuki Akiyama; Masahiko Ishida; Satoshi Inoue, all of Kyoto, Japan

[73] Assignee: Horiba, Ltd., Kyoto, Japan

[21] Appl. No.: 342,247

[22] Filed: Nov. 18, 1994

[30] Foreign Application Priority Data

Nov. 20, 1993 [JP] Japan .................. 5-066724 U
Dec. 31, 1993 [JP] Japan .................. 5-354288

[51] Int. Cl.$^6$ .............. G01J 5/08; G01N 21/61
[52] U.S. Cl. .......... 250/345; 250/343; 250/349; 250/373; 250/339.06; 250/339.12; 250/339.13
[58] Field of Search ................. 250/345, 343, 250/349, 373, 339.06, 339.12, 339.13

[56] References Cited

U.S. PATENT DOCUMENTS

| | | | |
|---|---|---|---|
| 4,271,124 | 6/1981 | Speeter | 250/345 |
| 4,355,233 | 10/1982 | Warnke et al. | 250/343 |
| 4,514,635 | 4/1985 | Ishida et al. | 250/343 |
| 4,687,337 | 8/1987 | Stewart et al. | 250/345 |
| 4,794,255 | 12/1988 | Miyatake et al. | 250/345 |
| 4,914,719 | 4/1990 | Conlon et al. | 250/343 |
| 5,092,342 | 3/1992 | Hattendorff et al. | 250/345 |
| 5,153,436 | 10/1992 | Apperson et al. | 250/345 |
| 5,331,409 | 7/1994 | Thurtell et al. | 250/345 |
| 5,332,901 | 7/1994 | Eckles et al. | 250/343 |

FOREIGN PATENT DOCUMENTS

| | | |
|---|---|---|
| 3026953 | 7/1980 | Germany . |
| 3544015 | 12/1985 | Germany . |
| 979850 | 5/1961 | United Kingdom . |

Primary Examiner—Constantine Hannaher
Assistant Examiner—Virgil Orland Tyler
Attorney, Agent, or Firm—Poms, Smith, Lande & Rose

[57] ABSTRACT

A gas analyzer capable of simultaneously detecting two or more components in a single-cell mode and a gas-analyzing mechanism suitable for simultaneously detecting two or more components in a cross-flow modulation single-cell mode are provided. A gas analyzer unit includes two measuring cells, light sources provided on one end side of each of the measuring cells, gas filter cells with interferential gaseous components hindering a detection of components to be measured enclosed provided on the other end side of each of the measuring cells, beam splitters included in two gas filter cells, first- and fourth and second- and third detectors provided on the side of transmitting position and the side of reflecting position, respectively, of each of the beam splitters and a sampling device connected with a rotary valve.

18 Claims, 3 Drawing Sheets

GAS ANALYZER AND GAS-ANALYZING MECHANISM

BACKGROUND OF THE INVENTION

1. Field of the Invention

The present invention relates to a gas analyzer and a gas-analyzing mechanism, in particular to an improvement of a non dispersive infrared analyzer capable of simultaneously detecting a plurality of components in a single-cell mode and a gas analyzer unit suitable for simultaneously detecting a plurality of components in a cross-flow modulation single-cell mode where a plurality of non dispersive infrared analyzers are used in combination.

2. Description of the Prior Art

A non dispersive infrared analyzer (hereinafter referred to as NDIR) has been generally used in a single-optical path single-component detection mode. In the case where a plurality of components are measured, even in case of a single-cell mode, two-optical path two-component detection mode is adopted and as a result, a large number of optical parts are required. In addition, in order to simultaneously measure 3 components or 4 components, even though a cross-flow modulation single-cell mode, in which a sample gas and a reference gas are alternately introduced into two cells through a rotary valve, is used, it is necessary to prepare two gas analyzer units and two series of flow rate of said sample gas from a sampling device. Consequently, not only for example a sampling flow rate is increased, a number of optical parts being increased, and a sampling system being complicated and thus manufacturing expenses are increased but also the maintenance of a plurality of analyzers is required and thus also a running cost is increased. In addition, in a light-intermitting mode, a problem has occurred also in for example a response-delay (in case of being connected in series).

SUMMARY OF THE INVENTION

The present invention has been achieved in view of the above described matters and it is an object of the present invention to provide a gas analyzer capable of simultaneously detecting a plurality of components in a single-cell mode and a gas-analyzing mechanism suitable for simultaneously detecting a plurality of components in a cross-flow modulation single-cell mode.

The present invention is particularly characterized in that a gas filter cell with interferential gaseous components hindering a detection of components to be measured enclosed therein is used so that a beam splitter may be included in said gas filter cell to divide a change in quantity of light absorbed by said components to be measured within the cell into the respective detectors by means of said beam splitter and the gas filter cell may be provided with a optical filter at an angle (for example 45° relatively to the direction of optical path) on the side of the cell further from a position where the conventional optical filter is arranged in parallel to a cell surface included therein and at least two gas filter cells with said optical filter included may be arranged in series on one optical path to measure the components to be measured in turn from one having the largest infrared energy (in turn from the component having the smallest wavelength ahead on said optical path) by means of the respective detectors or measure the components to be measured in turn from one having the smallest infrared energy (in turn from the component having the longest wavelength ahead on the optical path).

A gas analyzer according to the present invention is characterized in that a cell, in which the sample gas is to be introduced, is provided with a light source on one end side thereof and a gas filter cell with interferential gaseous components hindering a detection of components to be measured enclosed on the other end side thereof, said gas filter cell being provided with a beam splitter included therein, and a detector being provided on the side of transmitting position and the side of reflecting position of said beam splitter, respectively.

That is to say, according to the present invention, the beam splitter is provided on the other end side of the cell on an optical axis of a single-cell bench, so that not only a first detector measuring a first component to be measured can be arranged on the side of transmitting position on said optical axis but also a second detector measuring a second component to be measured can be arranged on the side of reflecting position on the optical axis and thus two components to be measured can be simultaneously detected in the single-cell mode. Moreover, the interferential gaseous components hindering the detection of said first and second components to be measured are enclosed within the gas filter cell with the beam splitter included, so that influences by the interferential components can be eliminated.

Furthermore, according to the present invention, from another viewpoint, a gas-analyzing mechanism, characterized in that 4 components are measured by a gas analyzer unit comprising two measuring cells, into which said sample gas and a reference gas are alternately introduced through a change-over valve, light sources provided on one end side of each of said measuring cells, the gas filter cells with the interferential gaseous components hindering the detection of the components to be measured enclosed provided on the other end side of each of the measuring cells, the beam splitters included in two gas filter cells and two detectors provided on the side of transmitting position and the side of reflecting position and a sampling device connected with said change-over valve, is provided.

That is to say, according to the present invention, the beam splitter is provided on the other end side of each of two measuring cells, so that 4 detectors in total can be arranged on the side of transmitting position and the side of reflecting position of the respective beam splitters. Consequently, the sample gas and said reference gas are alternatively sent in two measuring cells in the cross-flow modulation single-cell mode and thus at most 4 components can be simultaneously measured by means of 2 measuring cells. In addition, the sample gas can be disposed by means of one system of sampling device. Although two gas analyzer units and two sampling systems have been required for the conventional measurement of 4 components in the cross-flow modulation single-cell mode, according to the present invention, the measurement can be achieved by means of one gas analyzer unit and one sampling system. Moreover, the interferential gaseous components hindering the detection of the respective components to be measured are enclosed in the gas filter cells with the beam splitter included, so that said influences by the interferential components can be eliminated.

Besides, according to the present invention, from a further viewpoint, a gas-analyzing mechanism, characterized in that 3 components are measured by the gas analyzer unit comprising two measuring cells, into which the sample gas and the reference gas are alternately introduced through the change-over valve, the light sources provided on one end side of each of the measuring cells, the gas filter cell with the interferential gaseous components hindering the detection of the components to be measured enclosed provided on the other end side of one of the measuring cells, the beam splitter included in the gas filter cell and two detectors provided on the side of transmitting position and the side of reflecting position and the sampling device connected with the change-over valve, is provided.

That is to say, according to the present invention, the beam splitter is provided on the other end side of one of two measuring cells, so that three detectors in total, that is one on the side of transmitting side and the reflecting side, respectively, of the beam splitter and one on the other end side of the other measuring cell, can be arranged. Consequently, the sample gas and the reference gas are alternately sent in two measuring cells in the cross-flow modulation single-cell mode and thus at most 3 components can be simultaneously measured by means of 2 measuring cells. In addition, the sample gas can be disposed by means of one system of sampling device. Although two gas analyzer units and two sampling systems have been required for the conventional measurement of 3 components in the cross-flow modulation single-cell mode, according to the present invention, the measurement can be achieved by means of one gas analyzer unit and one sampling system. Moreover, the interferential gaseous components hindering the detection of the respective components to be measured are enclosed in the gas filter cells with the beam splitter included, so that said influences by the interferential components can be eliminated.

On the other hand, according to the present invention, from a view point that a large number of wavelength components are measured by means of one optical system, a gas analyzer, characterized in that the light source is provided on one end side of the cell, into which the sample gas is introduced, while, the gas filter cell with the interferential gaseous components hindering the detection of the components to be measured enclosed is provided on the other end side of the cell, an optical filter for obtaining a spectrum of infrared wavelengths being included in the gas filter cell, a plurality of gas filter cells with said optical filter included being arranged on one optical path, the detector being provided on the side of reflecting position of every gas filter cell, and one detector being provided on the side of transmitting side of the last gas filter cell, is provided.

That is to say, although the optical filter has been conventionally arranged in parallel to the surface of the cell (sample cell) of the gas analyzer between the cell and the detector in the gas analyzer to be used for reducing the interference, according to the present invention, not only the optical filter is provided at an angle (for example 45°) on the cell side further from the position of the conventional optical filter to obtain said spectrum of infrared energies emitted from the light source, whereby making the measurement of the components to be measured for the spectral wavelengths possible but also a large number of components can be measured by means of one optical system by shifting the wavelengths in turn by means of the optical filter.

In addition, according to the present invention, in order to measure three wavelength components, a gas-analyzing mechanism, characterized in that three wavelength components are measured by a gas analyzer unit comprising a measuring cell, into which the sample gas is introduced, a light source provided on one end side of said measuring cell, two gas filter cells with the interferential gaseous components hindering the detection of the components to be measured enclosed arranged in series on an optical path on the other end side of the measuring cell, optical filters for obtaining a spectrum of infrared wavelengths included in the respective gas filter cells, two detectors provided on the side of reflecting position of the respective gas filter cells and one detector provided on said optical path on the side of transmitting position and a sampling device connected with the measuring cell, is provided.

That is to say, in order to measure three wavelength components, short-wavelength optical filters (for use in cutting-on) or long-wavelength optical filters (for use in cutting-off) are arranged on the side close to said light source, cutting positions of the optical filters being able to be slid in turn toward a long-wavelength side (or a short-wavelength side) as their positions make rearward progress on one optical path, and said wavelengths shorter than a wavelength (a) being reflected by a surface of the first optical filter, so that said infrared energies shorter than said wavelength (a) are incident upon said detector. Successively, infrared rays transmitting through the first optical filter are sent to the following optical filter where the wavelengths shorter than a wavelength (b) are similarly reflected by a surface of the following optical filter, so that the infrared energies shorter than said wavelength (b) are incident upon the further detector and the rest is reflected to be incident upon the still further detector. Thus, the spectrum of three components to be measured can be obtained.

Besides, according to the present invention, in order to measure four wavelength components, a gas-analyzing mechanism, characterized in that four wavelength components are measured by a gas analyzer unit comprising a measuring cell, into which the sample gas is introduced, a light source provided on one end side of said measuring cell, three gas filter cells with the interferential gaseous components hindering the detection of the components to be measured enclosed arranged in series on an optical path on the other end side of the measuring cell, optical filters for obtaining a spectrum of infrared wavelengths included in the respective gas filter cells, three detectors provided on the side of reflecting position of the respective gas filter cells and one detector provided on said optical path on the side of transmitting position and a sampling device connected with the measuring cell, is provided.

DETAILED DESCRIPTION OF THE PREFERRED EMBODIMENTS

The preferred embodiments of the present invention will be below described with reference to the drawings. In addition, the present invention is not limited by the preferred embodiments.

Figure 1:
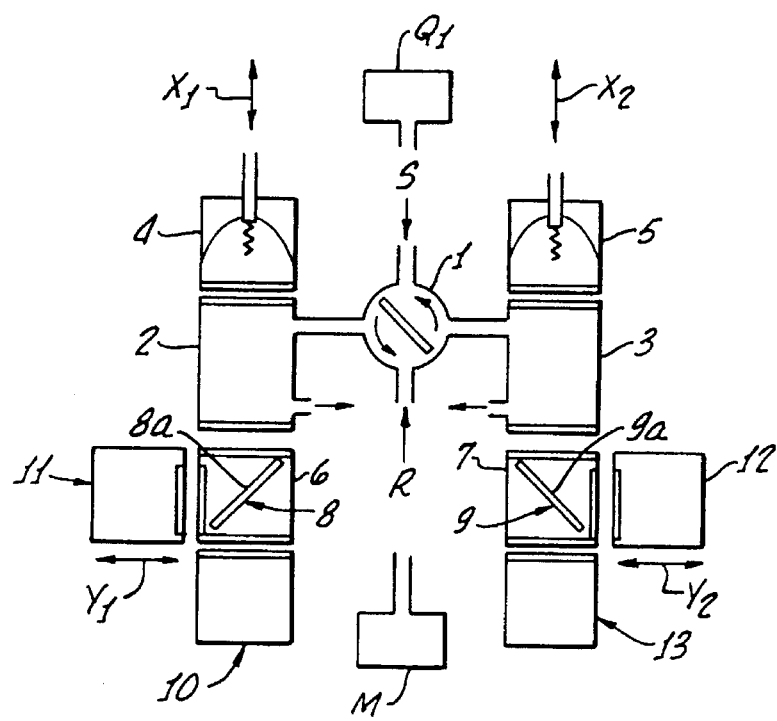
FIG. 1 is a total block diagram showing a first preferred embodiment of the present invention.

FIG. 1 shows a first preferred embodiment of the present invention. That is to say, FIG. 1 shows a gas-analyzing mechanism in the case where at most four components are simultaneously measured by means of two measuring cells in a cross-flow modulation single-cell mode.

Referring to FIG. 1, in said gas-analyzing mechanism, said four components are measured by a gas analyzer unit comprising two measuring cells 2, 3, into which a sample gas S and a reference gas R are alternately introduced through a rotary valve (change-over valve) 1, light sources 4, 5 provided on one end side of each of said measuring cells 2, 3, gas filter cells 6, 7 with interferential gaseous components hindering a detection of components to be measured enclosed provided on the other end side of each of the measuring cells 2, 3, beam separators such as beam splitters 8, 9 included in said gas filter cells 6, 7 and first and fourth detectors 10, 13 and second and third detectors 11, 12 provided on the side of transmitting position and the side of reflecting position of the respective beam splitters 8, 9 and a sampling device $Q_1$ connected with said rotary valve 1. In addition, a mark M designates a refiner for producing said reference gas.

Furthermore, the beam splitters 8, 9 are provided within the gas filter cells 6, 7 with transmitting and reflecting surfaces 8a, 9a thereof having an angle of inclination of 45° relatively to optical axes $X_1$, $X_2$, of the respective measuring cells 2, 3 and said first and fourth detector 10, 13 measuring a first and fourth component to be measured, respectively, is arranged on said optical axis $X_1$, $X_2$, respectively, while said second and third detector 11, 12 measuring a second and third component to be measured is arranged on a 90° reflecting optical axis $Y_1$, $Y_2$, respectively.

And, although a splitting ratio of quantity of light into the first and second detectors 10, 11 by means of the beam splitter 8 and the third and fourth detectors 12, 13 by means of the beam splitter 9 is usually set at 1:1, in the case where there are characteristic differences between the detectors in sensitivity, reflection factors are adjusted to set said splitting ratio at 1:2 or more, whereby distributing said quantity of light in correspondence to detecting sensitivities of both detectors.

Since the present preferred embodiment has the above described construction, the sample gas S and the reference gas R are alternately introduced into the measuring cell 2 or the measuring cell 3. The sample gas S is disposed by means of one system of sampling device $Q_1$. A change in quantity of light absorbed by the components to be measured within the measuring cells 2, 3 is equally split into the respective detectors 10 to 13 by means of the beam splitters 8, 9 to amplifiedly put out a signal of each detector.

At this time, said interferential gaseous components hindering said detection of each component to be measured are enclosed in the gas filter cells 6, 7 with the beam splitters 8, 9 included to eliminate influences by the interferential components. For example, in a measurement of stack gas, in the case where $NO_2$ or $SO_2$ is measured, $CO_2$ is enclosed in the gas filter cells.

According to the present preferred embodiment, since the beam splitter 8, 9 is provided on the other end side of the measuring cell 2, 3, respectively, in the above described manner, four detectors 10 to 13 in total can be arranged on the side of transmitting position and the side of reflecting position of the respective beam splitters. Consequently, the sample gas S and the reference gas R can be alternately introduced into two measuring cells 2, 3 in the cross-flow modulation single-cell mode to be able to simultaneously measure at most four components by means of two measuring cells. In addition, the sample gas S can be disposed by means of one system of sampling device $Q_1$. Although two gas analyzer units and two sampling systems have been required for the conventional measurement of four components in the cross-flow modulation single-cell mode, according to the present preferred embodiment, the measurement can be achieved by means of one gas analyzer unit and one sampling system $Q_1$. Moreover, the interferential gaseous components hindering the detection of the respective components to be measured are enclosed in the gas filter cells 6, 7 with the beam splitters 8, 9 included to be able to eliminate the influences by the interferential components. Besides, also said refiner M for producing the reference gas does not complicate the gas-analyzing mechanism in the same manner as the sampling system $Q_1$.

Figure 2:
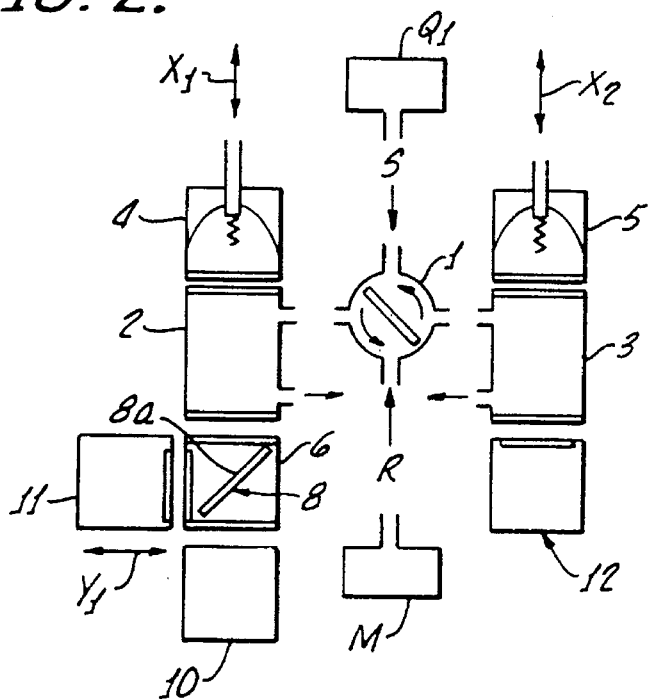
FIG. 2 is a total block diagram showing a second preferred embodiment of the present invention.

FIG. 2 shows a second preferred embodiment of the present invention. That is to say, FIG. 2 shows a gas-analyzing mechanism in the case where at most three components are simultaneously measured by means of two measuring cells in a cross-flow modulation single cell-mode.

Referring to FIG. 2, in said gas-analyzing mechanism, said three components are measured by a gas analyzer unit comprising two measuring cells 2, 3, into which a sample gas S and a reference gas R are alternately introduced through a rotary valve (change-over valve) 1, light sources 4, 5 provided on one end side of each of said measuring cells 2, 3, a gas filter cell 6 with interferential gaseous components hindering a detection of components to be measured enclosed provided on the other end side of one measuring cell 2 of the measuring cells 2, 3, a beam splitter 8 included in said gas filter cell 6, two detectors 10, 11 provided on the side of transmitting position and the side of reflecting position of said beam splitter 8 and one detector 12 provided on the other end side of the other measuring cell 3 and a sampling device $Q_1$ connected with said rotary valve 1.

Furthermore, the beam splitters 8 is provided within the gas filter cell 6 with a transmitting reflecting surface 8a thereof having an angle of inclination of 45° relatively to an optical axis $X_1$ of the measuring cell 2, said first detector 10 measuring a first component to be measured being arranged on said optical axis $X_1$, and said second detector 11 measuring a second component to be measured being arranged on a 90° reflecting optical axis $Y_1$ while a third detector 12 is arranged on an optical axis $X_2$ on the other end side of the other measuring cell 3. And, although a splitting ratio of quantity of light into the first and second detectors 10, 11 by means of the beam splitter 8 is usually set at 1:1, in the case where there are characteristic differences between the detectors in sensitivity, reflection factors are adjusted to set said splitting ratio at 1:2 or more, whereby distributing said quantity of light is correspondence to detecting sensitivities of both detectors.

Since the present preferred embodiment has the above described construction, the sample gas S and the reference gas R are alternately introduced into the measuring cell 2 or the measuring cell 3. The sample gas S is disposed by means of one system of sampling device $Q_1$. A change in quantity of light absorbed by the components to be measured within the measuring cell 2 is equally split into the respective detectors 10, 11 by means of the beam splitter 8 to amplifiedly put out a signal of each detector. On the other hand, a change in quantity of light absorbed by the components to be measured within the measuring cell 3 is directly received by said third detector 12 to amplifiedly put out a signal of the third detector 12.

At this time, said interferential gaseous components hindering said detection of each component to be measured are enclosed in the gas filter cell 6 with the beam splitters 8 included to eliminate influences by the interferential components. For example, in a measurement of stack gas, in the case where $NO_2$ or $SO_2$ is measured, $CO_2$ is enclosed in the gas filter cell.

According to the present preferred embodiment, since the beam splitter 8 is provided on the other end side of one measuring cell 2 of two measuring cells 2, 3 in the above described manner, three detectors in total, that is one detector 10 on the side of transmitting position of the beam splitter 8, one detector 11 on the side of reflecting position of the beam splitter 8 and one detector 12 on the other end side of the other measuring cell 3, can be arranged. Consequently, the sample gas S and the reference gas R can be alternately introduced into two measuring cells 2, 3 in the cross-flow modulation single-cell mode to be able to simultaneously measure at most three components by means of two measuring cells. In addition, the sample gas S can be disposed by means of one system of sampling device $Q_1$. Although two gas analyzer units and two sampling systems have been required for the conventional measurement of three components in the cross-flow modulation single-cell mode, according to the present preferred embodiment, the measurement can be achieved by means of one gas analyzer unit and one sampling system $Q_1$. Moreover, the interferential gaseous components hindering the detection of the respective components to be measured are enclosed in the gas filter cell 6 with the beam splitter 8 included to be able to eliminate the influences by the interferential components.

Figure 3:
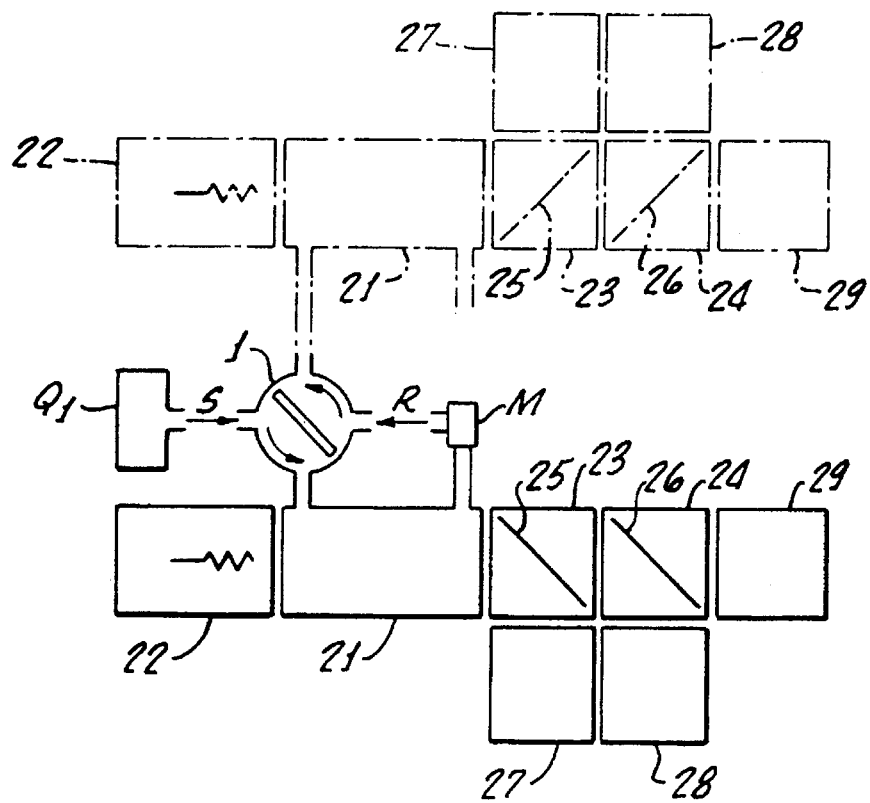
FIG. 3 is a total block diagram showing a third preferred embodiment of the present invention.

FIG. 3 shows a third preferred embodiment of the present invention. That is to say, FIG. 3 shows a gas-analyzing mechanism for use in a measurement of concentrations of three components (for example CO, NO and $SO_2$) by a cross-flow modulation mode. A cross-flow modulation gas analyzer is typically provided with a rotary valve to switch gas streams. The rotary valve alternatively switches the sample gas and the zero gas (reference gas, standard gas) between two cells of the analyzer on a fixed time cycle. Consequently, each of the two cells alternatively function as a sample cell and a reference cell. Cross-flow modulation analyzers are substantially free of deficiencies characteristic of conventional gas analyzers (e.g., zero drift) and further may provide expanded dynamic range.

Referring to FIG. 3, said gas-analyzing mechanism comprises a measuring cell 21, into which a sample gas S and a reference gas R are alternately introduced, a light source 22 provided on one end side of said measuring cell 21, two gas filter cells 23, 24 with interferential gaseous components hindering a detection of components to be measured enclosed arranged in series on an optical path on the other end side of the measuring cell 21, beam separators in the form of optical filters 25, 26 for obtaining a spectrum of infrared wavelengths included in the respective gas filter cells 23, 24, two detectors 27, 28 provided on the side of reflecting position of the respective gas filter cells and one detector 29 provided on said optical path on the side of transmitting position and a sampling device Q, connected with the measuring cell 21 into which said sample gas S and said reference gas R are alternately introduced through a rotary valve (change-over valve) 1.

Since said third preferred embodiment has the above described construction, in order to measure three wavelength components, short-wavelength optical filters 25, 26 are arranged in turn from a side closer to said light source 22, cutting positions of the optical filters 25, 26 being able to be slid in turn toward a long-wavelength side as their positions make rearward progress on one optical path, and said wavelengths shorter than a wavelength (a) being reflected by a surface of the first optical filter 25, so that infrared energies shorter than said wavelength (a) are incident upon said detector 27. Successively, infrared rays transmitting through the first optical filter 25 are sent to the following optical filter 26 where the wavelengths shorter than a wavelength (b) are similarly reflected by a surface of the following optical filter 26, so that the infrared energies shorter than said wavelength (b) are incident upon the further detector 28 and the rest is reflected to be incident upon the still further detector 29 provided on the optical path. Thus, the spectrum of three components to be measured can be obtained.

Figure 4:
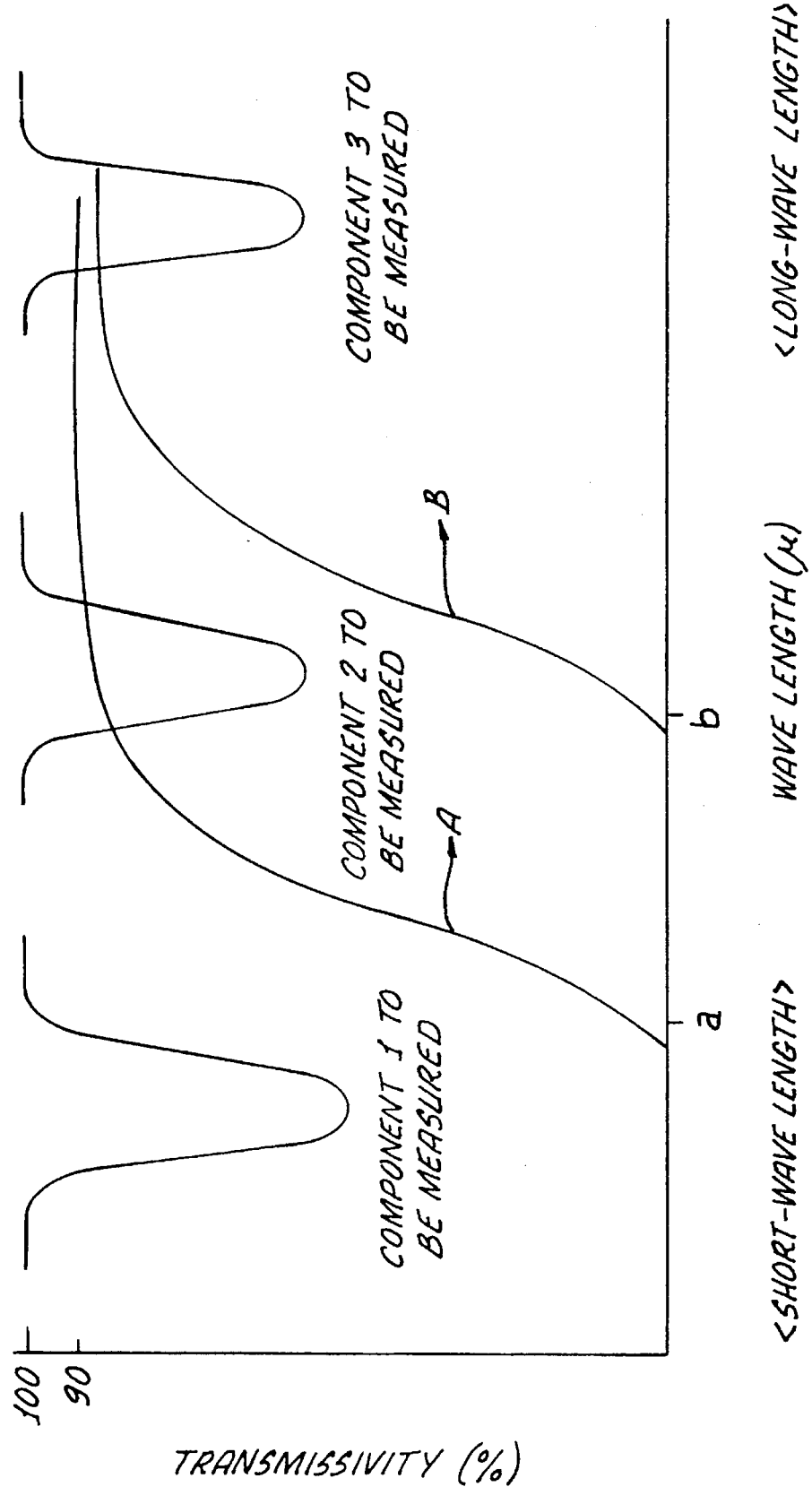
FIG. 4 is a characteristic drawing showing transmissivities of optical filters.

At this time, in the detector 27, the components having infrared absorptions at positions shown in FIG. 4 are objects to be measured. As to a spectral capacity of the optical filter 25, for example, if the maximum transmissivity of the optical filter 25 is 90%, 90% of the infrared energies within a long-wavelength range excepting a wavelength range for a component to be measured is transmitted to the rear optical filter 26 from the light source 22 and the rest is reflected to be incident upon the detector 27. That is to say, since the transmissivity of the optical filter 25 for the wavelengths on the wavelength side shorter than the wavelength (a) is nearly 0, they are transmitted to the detector 27 without loss. Also in the optical filter 26, since the transmissivity of the optical filter 26 for the wavelengths on the wavelength side shorter than the wavelength (b) is nearly 0, they are transmitted to the detector 28 without loss. Thus, the spectrum can be obtained in the same manner as in the optical filter 25. After all, the spectrum of the component to be measured 1, 2 is obtained in the optical filter 25, 26, respectively, to be detected by means of the detector 27, 28, respectively, while the rest, that is the third component 3, is detected by means of the detector 29. Moreover, the optical filter 25 has filter characteristics shown by a curve A and the optical filter 26 has filter characteristics shown by a curve B.

As above described, according to the third preferred embodiment, three detectors in total, that is the detector 27, 28 on the side of reflecting position of each of the optical filters 25, 26 and one detector 29 on the side transmitting position of the optical filters 25, 26, can be arranged. Consequently, the sample gas S and the reference gas R can be alternately introduced into one measuring cell 21 to be able to simultaneously measure three components by means of one measuring cell in the liquid modulation single-cell mode. In addition, the sample gas S can be disposed by means of one system of sampling device $Q_1$. Although the optical filters have been arranged in parallel to the surface of the measuring cell between the measuring cell and the detectors to reduce the interference, so that two gas analyzer units and two sampling systems have been required, for the conventional measurement of three components, according to the present preferred embodiment, the short-wavelength optical filters 25, 26 are arranged in turn from said side closer to the light source 22 and said cutting positions of the optical filters 25, 26 are slid in turn toward said long-wavelength side as their positions make rearward progress, so that the measurement can be achieved by means of one gas analyzer unit and one sampling system $Q_1$. Moreover, the interferential gaseous components hindering the detection of the respective components to be measured are enclosed in the gas filter cell 23, 24 with the optical filter 25, 26, respectively, included to be able to eliminate the influences by the interferential components.

In short, a plurality of components (for example CO, NO and $SO_2$) can be measured in the gas-analyzing mechanism having one optical system. In addition, since the infrared energies, which have been cut by means of the optical filter in the conventional measurement, are used as the energies for other measurements, so that the gas-analyzing mechanism, which is compact, inexpensive and reduced in sensitivity-loss, can be provided. Furthermore, although the cell has been increased in diameter due to a size of a sensor and thus the sample has been increased in flow rate or the energy has been lost in the case where semiconductors or pyroelectric elements are arranged for a plurality of components in one cell, according to the present invention, the measurement can be achieved by the use of the cell having the conventional size for use in the measurement of one components.

Besides, in the above described third preferred embodiment, as shown by an imaginary line in FIG. 3, a gas analyzer unit is added through the rotary valve 1 to construct a pair of gas analyzer units, whereby being able to measure six wavelength components.

Figure 5:
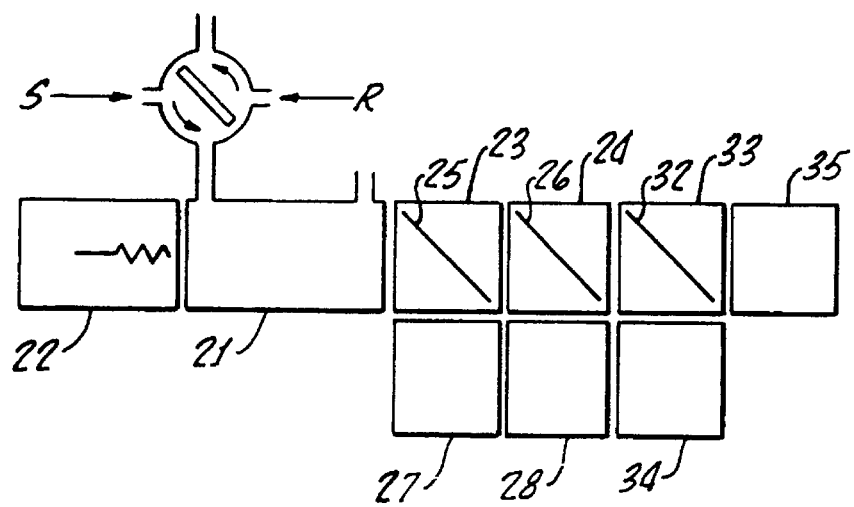
FIG. 5 is a total block diagram showing a fourth preferred embodiment of the present invention.

FIG. 5 shows a fourth preferred embodiment of the present invention, in which four wavelength components are measured by a gas analyzer unit comprising a measuring cell 21, into which a sample gas S and a reference gas R are alternately introduced, a light source 22 provided on one end side of said measuring cell 21, three gas filter cells 23, 24, 33 with interferential gaseous components hindering a detection of components to be measured enclosed provided in turn on an optical path on the other end side of the measuring cell 21, optical filter 25, 26, 32 included in each of said gas filter cells 23, 24, 33 for obtaining a spectrum of infrared wavelengths, three detectors 27, 28, 34 provided on the side of reflecting position of the respective gas filter cells 23, 24, 33 and one detector 35 provided on said optical path on the side of transmitting position of the respective gas filter cells 23, 24, 33 and a sampling device connected with the measuring cell 21.

Also according to this preferred embodiment, a plurality of components can be measured by means of one optical system. That is to say, three optical filters 25, 26, 33 are arranged at an angle (for example 45°) on the side closer to the cell from the positions of optical filters in the conventional measurement to obtain a spectrum of energies emitted from said light source 22, whereby shifting spectral wavelengths in turn by means of the optical filters to be able to measure the components to be measured for said spectral wavelengths.

In addition, a pneumatic detector, a pyroelectric detector, a thermopile, a semiconductor sensor and the like can be used as the detector in the above described preferred embodiments. Furthermore, the optical filter in the above described third and fourth preferred embodiments can be used for the cutting-off in addition to the cutting-on. In this case, an optical system for measuring the components on the long-wavelength side is constructed ahead.

As above described, according to the present invention, the beam splitter is provided on the other end side of the cell, so that not only the first detector measuring the first component to be measured can be arranged on the side of transmitting position on the optical axis but also the second detector measuring the second component to be measured can be arranged on the side of the reflecting optical axis and thus two components to be measured can be simultaneously detected in the single-cell mode. Moreover, the interferential gaseous components hindering the detection of the first and second components to be measured are enclosed in the gas filter cells with the beam splitter included to be effective for the detection of both components to be measured.

Besides, the beam splitter is provided on the other end side of each of two measuring cells, so that four detectors in total, that is two detectors on the side of transmitting position of the respective beam splitters and two detectors on the side of reflecting position of the respective beam splitters, can be arranged. Consequently, the sample gas S and the reference gas R can be alternately introduced into two measuring cells through the rotary valve to be able to simultaneously measure at most four components by means of two measuring cells. In addition, the sample gas can be disposed by means of one system of sampling device. Although two gas analyzer units and two sampling systems have been required for the conventional measurement of four components in the cross-flow modulation single-cell mode, according to the present invention, the measurement can be achieved by means of one gas analyzer unit and one sampling system. Moreover, the interferential gaseous components hindering the detection of the respective components to be measured are enclosed in the gas filter cells with the beam splitter included, so that said influences by the interferential components can be eliminated.

Besides, since the beam splitter is provided on the other end side of one measuring cell of two measuring cells, three detectors in total, that is one detector on the side of transmitting position of the beam splitter, one detector on the side of reflecting position of the beam splitter and one detector on the other end side of the other measuring cell, can be arranged. Consequently, the sample gas and the reference gas can be alternately introduced into two measuring cells in the cross-flow modulation single-cell mode to be able to simultaneously measure at most three components by means of two measuring cells. In addition, the sample gas can be disposed by means of one system of sampling device. Although two gas analyzer units and two sampling systems have been required for the conventional measurement of three components in the cross-flow modulation single-cell mode, according to the present invention, the measurement can be achieved by means of one gas analyzer unit and one sampling system $Q_1$. Moreover, the interferential gaseous components hindering the detection of the respective components to be measured are enclosed in the gas filter cell with the beam splitter included to be able to eliminate the influences by the interferential components.

In short, although two gas analyzers and two sampling systems have been required for the conventional measurement of three or four components in the cross-flow modulation single-cell mode, according to the present invention, the measurement can be achieved by means of one gas analyzer unit and one sampling system. Thus, not only the manufacturing expenses of products can be reduced but also the sampling system can be simplified to make the maintenance easy. In addition, also the refiner for producing the reference gas does not complicate the gas analyzing mechanism in the same manner as the sampling system.

In addition, according to the present invention, a plurality of optical filters are arranged at an angle on the side closer to the cell from the positions of optical filters in the conventional measurement to obtain a spectrum of energies emitted from the light source, whereby shifting spectral wavelengths in turn by means of the optical filters to be able to construct the optical system capable of efficiently obtaining the spectrum of the aimed wavelengths of the components to be measured and achieving the measurement of a plurality of components, and thus the gas analyzer can be compactized. That is to say, a plurality of components can be measured in the gas analyzer having one optical system. In addition, since the infrared energies, which have been cut by means of the optical filter in the conventional measurement, are used as the energies for other measurements, so that the gas analyzer, which is compact, inexpensive and reduced in sensitivity-loss, can be provided. Furthermore, although the cell has been increased in diameter due to a size of a sensor and thus the sample has been increased in flow rate or the energy has been lost in the case where semiconductors or pyroelectric elements are arranged for a plurality of components in one cell, according to the present invention, the measurement can be achieved by the use of the cell having the conventional size for use in the measurement of one component. Moreover, the interferential gaseous components hindering the detection of the respective components to be measured are enclosed in the gas filter cells with the optical filter included to be effective for the detection of the respective components to be measured.

What is claimed is:

1. A gas analyzer with a measuring cell into which a sample gas is to be introduced, the measuring cell including one end side and a second end side, the gas analyzer comprising:

a light source on the one end side of the measuring cell;

a gas filter cell on the second end side of the measuring cell, said gas filter cell having interferential gaseous components hindering a detection of components to be measured enclosed therein, said gas filter cell including a light separator therein, said gas filter cell including a reflecting position and a transmitting position, said light separator for reflecting light from said light source to said reflecting position and for transmitting light from said light source to said transmitting position; and a first detector for said reflecting position and for measuring a first component of the sample gas, and a second detector for said transmitting position and for measuring a second component of the sample gas.

2. The gas analyzer of claim 1 wherein said light separator includes a beam splitter.

3. The gas analyzer of claim 2 wherein said beam splitter is characterized by a reflection factor which is different from 1:1.

4. The gas analyzer of claim 2 wherein said first detector faces a transmitting surface on said gas filter cell and said second detector faces a reflecting surface on said gas filter cell and said light source defines an optical path and said reflecting and transmitting surfaces have an angle of inclination of approximately 45° relative to the optical path.

5. The gas analyzer of claim 1 wherein said light separator includes an optical filter.

6. A gas analyzer unit in a gas-analyzer mechanism for measuring a plurality of components, the gas analyzer unit comprising:

two measuring cells into which a sample gas and a reference gas are alternatively introduced through a change-over valve which is connected to a sampling device, each of the measuring cells including one end side and a second end side;

light sources provided on said one end side of each of said measuring cells;

one gas filter cell provided on said second end side of one of said measuring cells, said one gas filter cell having interferential gaseous components hindering a detection of components to be measured enclosed therein, said one gas filter cell including an optical filter therein, said one gas filter cell including a reflecting position and a transmitting position, said optical filter for reflecting light from one of said light sources to said reflecting position and for transmitting light from said one of said light sources to said transmitting position; and a plurality of detectors including a detector for said reflecting position and a detector for transmitting position, each of said detectors for measuring a component of the sample gas.

7. The gas analyzer unit of claim 6 further comprising:

a second gas filter cell provided on said second end side of the other measuring cell, said second gas filter cell having interferential gaseous components hindering a detection of components to be measured enclosed therein, said second gas filter cell including an optical filter therein, said second filter cell including a reflecting position and a transmitting position, said optical filter of said second gas filter cell for reflecting light from another one of said light sources to said reflecting position and for transmitting light from said another one of said light sources to said transmitting position;

said plurality of detectors further including a detector for said reflecting position and a detector for said transmitting position of said second gas filter cell, whereby four components are measured by the gas analyzer unit.

8. The gas analyzer of claim 7 wherein said plurality of detectors comprise:

a first detector facing a transmitting surface of said one gas filter cell;

a second detector facing a reflecting surface of said one gas filter cell;

a third detector facing a reflecting surface of said second gas filter cell; and a fourth detector facing a transmitting surface of said second gas filter cell.

9. The gas analyzer of claim 8 wherein said light source defines an optical path and said reflecting and transmitting surfaces of said one gas filter cell and said second gas filter cell have angles of inclination of approximately 45° relative to the optical path.

10. The gas analyzer unit of claim 6 wherein said plurality of detectors further comprise one detector provided on said second end side of said measuring cell without said one gas filter cell, whereby three components are measured by the gas analyzer unit.

11. The gas analyzer of claim 10 wherein said detectors for said reflecting position and said transmitting position comprise:

a first detector facing a transmitting surface of said one gas filter cell; and a second detector facing a reflecting surface of said one gas filter cell.

12. The gas analyzer of claim 11 wherein said light source defines an optical path and said reflecting and transmitting surfaces have an angle of inclination of approximately 45° relative to the optical path.

13. A gas analyzer with a measuring cell into which a sample gas is to be introduced, the measuring cell including one end side and a second end side, the gas analyzer comprising:

a light source on the one end side of the measuring cell;

a plurality of gas filter cells on the second end side of the measuring cell, said gas filter cells being arranged in series along an optical path, said gas filter cells having interferential gaseous components hindering a detection of components to be measured enclosed therein, each of said gas filter cells including an optical filter for obtaining a spectrum of infrared wavelengths being included in said gas filter cell, each of said gas filter cells including a reflecting position and a transmitting position, said optical filter for reflecting light from said light source to said reflecting position and for transmitted light from said light source to said transmitting position; and a plurality of detectors for said reflecting positions of said gas filter cells and said transmitting position of a last gas filter cell along the optical path.

14. The gas analyzer of claim 13 wherein said plurality of gas filter cells successively transmit longer wavelength components toward said last gas filter cell.

15. A gas analyzer unit in a gas-analyzer mechanism for measuring a plurality of components, the gas analyzer unit comprising:

a measuring cell into which a sample gas is introduced via a sampling device, said measuring cell including one end side and a second end side;

a light source provided on said one end side of said measuring cell;

a plurality of gas filter cells provided on said second end side of said measuring cell, said gas filter cells being arranged in series along an optical path, said gas filter cells having interferential gaseous components hindering a detection of components to be measured enclosed therein, each of said gas filter cells including an optical filter for obtaining a spectrum of infrared wavelengths being included in said gas filter cell, each of said gas filter cells including a reflecting position and a transmitting position, said optical filter for reflecting light from said light source to said reflecting position and for transmitting light from said light source to said transmitting position; and a plurality of detectors for said reflecting positions of said gas filter cells and said transmitting position of a last gas filter cell along the optical path.

16. The gas analyzer unit of claim 15 wherein said plurality of gas filter cells successively transmit longer wavelength components toward said last gas filter cell.

17. The gas analyzer unit of claim 15 wherein said plurality of gas filter cells comprise two gas filter cells and said plurality of detectors comprise two detectors facing reflecting surfaces of said two gas filter cells and a third detector facing a transmitting surface of said last gas filter cell along the optical path, whereby three components are measured by the gas analyzer unit.

18. The gas analyzer unit of claim 15 wherein said plurality of gas filter cells comprise three gas filter cells and said plurality of detectors comprise three detectors facing reflecting surfaces of said three gas filter cells and a fourth detector facing a transmitting surface of said last gas filter cell along the optical path, whereby four components are measured by the gas analyzer unit.

* * * * *